United States Patent
Hehrlein et al.

(10) Patent No.: US 7,481,799 B2
(45) Date of Patent: Jan. 27, 2009

(54) DELIVERY SOURCE OF OXYGEN

(75) Inventors: Christoph Hehrlein, Freiburg (DE); Gerhard Karl Wolf, Heidelberg (DE); Adalbert Kovacs, Eppelheim (DE)

(73) Assignee: Oxira Medical Inc., Boca Raton, FL (US)

( * ) Notice: Subject to any disclaimer, the term of this patent is extended or adjusted under 35 U.S.C. 154(b) by 797 days.

(21) Appl. No.: 10/038,468

(22) Filed: Jan. 3, 2002

(65) Prior Publication Data

US 2003/0198798 A1    Oct. 23, 2003

(51) Int. Cl.
*A61M 5/00* (2006.01)

(52) U.S. Cl. .............. 604/264; 604/103.01; 604/103.02; 604/508

(58) Field of Classification Search .............. 604/890.1, 604/506–510, 96.01–103.05, 264–265, 289, 604/912–915, 21, 103.08; 606/192–194; 424/422–426; 428/313.5; 623/1.1, 1.11
See application file for complete search history.

(56) References Cited

U.S. PATENT DOCUMENTS

| | | | |
|---|---|---|---|
| 3,958,014 A | 5/1976 | Watanabe et al. | |
| 4,252,827 A | 2/1981 | Yokoyama et al. | |
| 4,366,169 A * | 12/1982 | White | 514/755 |
| 4,445,500 A | 5/1984 | Osterholm | |
| 4,636,195 A | 1/1987 | Wolinsky | |
| 4,795,423 A | 1/1989 | Osterhom | |
| 4,909,252 A | 3/1990 | Goldberger | |
| 4,944,745 A | 7/1990 | Sogard et al. | |
| 5,059,166 A | 10/1991 | Fischell et al. | |
| 5,084,011 A * | 1/1992 | Grady | 604/24 |
| 5,087,247 A | 2/1992 | Horn et al. | |
| 5,199,939 A | 4/1993 | Dake et al. | |
| 5,334,142 A * | 8/1994 | Paradis | 604/509 |
| 5,865,789 A * | 2/1999 | Hattler | 604/26 |
| 5,951,458 A | 9/1999 | Hastings et al. | |
| 6,048,332 A | 4/2000 | Duffy et al. | |
| 6,110,483 A * | 8/2000 | Whitbourne et al. | 424/423 |

(Continued)

FOREIGN PATENT DOCUMENTS

EP    0 112 658 A2    7/1984

(Continued)

OTHER PUBLICATIONS

Markus Ferrari et al. "Coronary Flow Analysis During Autoperfusion Angioplasty" Coronary Artery Disease Nov./Dec. 1997, vol. 8 No. 11/12, pp. 697-702 Rapid Science Publishers, USA.

(Continued)

*Primary Examiner*—Nicholas D Lucchesi
*Assistant Examiner*—Theodore J Stigell
(74) *Attorney, Agent, or Firm*—Pandiscio & Pandiscio

(57) ABSTRACT

The invention described herein consists of an oxygen deliver source for local blood or tissue oxygenation. The invention consists of porous polymer structures being part of a medical device from which a liquid oxygen carrier is locally or systemically released. The substrate membrane impregnated with the oxygen carrier may be a part of a tube, a balloon, a perfusion balloon, a stent and a wire. The substrate membrane is sealed with a removable housing for the oxygen carrier to allow storage of the medical device.

23 Claims, 3 Drawing Sheets

U.S. PATENT DOCUMENTS 6,146,358 A * 11/2000 Rowe .................... 604/103.02

FOREIGN PATENT DOCUMENTS

EP        0 372 088 A1    6/1990

WO        WO 97/32626    9/1997

OTHER PUBLICATIONS

Walter A. Tan et al. "Long-Term Clinical Outcomes After Unprotected Left Main Trunk Percutaneous Revascularization in 279 Patients" Circulation, Oct. 2, 2001, pp. 1609-1614, vol. 104, USA.

* cited by examiner

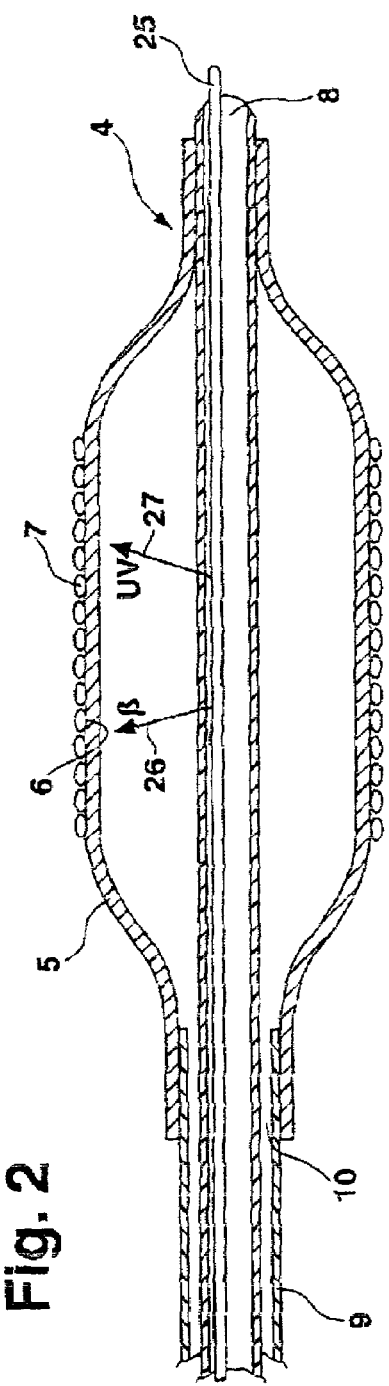
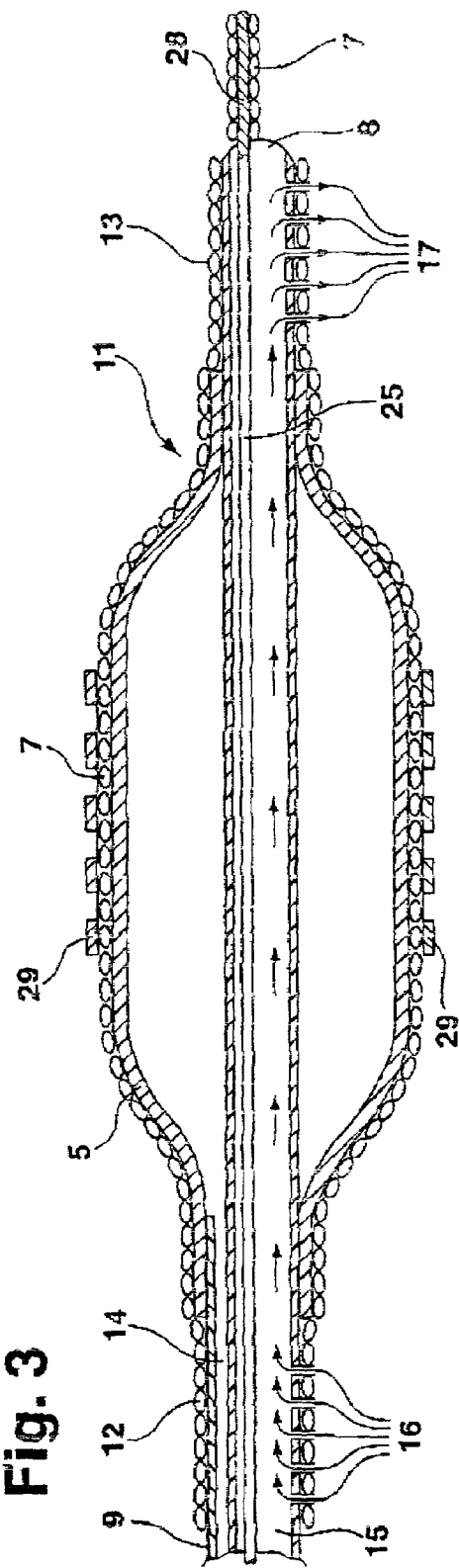
Fig. 2
Fig. 3

DELIVERY SOURCE OF OXYGEN

FIELD OF THE INVENTION

The invention relates to a percutaneously applicable oxygenating source for tissue and blood. The field of the invention is the treatment of cardiovascular disease. The material disclosed herein was conceived to reduce the risks of ischemic events during an angioplasty procedure, to improve healing of lacerated hypoxic tissues, and to slow down restenosis after vascular interventions.

BACKGROUND OF THE INVENTION

A percutaneous transluminal angioplasty (PTA) of blood vessels including the coronary arteries (PTCA) is a very popular method to eliminate vessel narrowing or stenosis that obstructs blood flow to human organs. The success rates of coronary angioplasty procedures is inversely related to the extent of the vascular disease, and the patients intolerance towards myocardial ischemia during temporary blood flow obstruction.

One of the principle limitations of a coronary angioplasty is the complete obstruction of blood flow during the inflation of the balloon. After a short period of balloon occlusion, patients experience ischemia due to the lack of flow of oxygenated blood to the myocardium. Myocardial ischemia is usually indicated by either angina pectoris or cardiac arrhythmias. In the past, several perfusion balloon catheters were developed to overcome the problem of blood flow obstruction during percutaneous coronary interventions. U.S. Pat. No. 4,944,745 (Sograd) discloses a perfusion balloon catheter that allows passive perfusion of blood through a catheter whose balloon is obstructing blood flow. U.S. Pat. No. 4,909,252 (Goldberger) discloses a perfusion balloon catheter with a central opening allowing blood flow passage when the balloon is fully inflated. U.S. Pat. No. 5,087,247 (Horn et al) discloses a balloon perfusion catheter with an elongated flexible perfusion shaft with multiple openings proximal and distal to the balloon to permit blood flow through an artery during balloon inflation. WO 9732626 (Cox et al) discloses an inflatable balloon envelope allowing blood passage during inflation of the device.

However, perfusion balloon catheters placed into small arteries such as the coronary circulation have the disadvantage of limited blood perfusion capacity inherent to relatively small blood flow rates in those arteries. In times of increasing rates of coronary stenting, perfusion balloon catheters have become obsolete. For instance, a prolongation of the balloon dilatation process to achieve better angioplasty results is not any more necessary. The dilemma of the perfusion balloon was characterized in a publication by Ferrari et al (Coron Art Dis 1997) who conclude their studies with the statement that in "high-risk patients dependent on adequate coronary perfusion, autoperfusion balloons are not able to provide sufficient distal coronary blood flow during balloon inflation". Insufficient blood flow distal to an inflated balloon causes hypoxia and ischemia of end organs because the oxygenation of tissue previously supplied with blood is reduced. Angioplasty is of high risk in patients who require dilatation of the unprotected trunk of the left main coronary artery. Tan et al (Circulation 2001) concluded that although percutaneous balloon interventions are a generally accepted treatment modality for coronary artery disease, left main PTCA remains are high risk procedure for the patient.

Another limitation of a coronary angioplasty is restenosis. Restenosis after PTCA has been successfully inhibited by ionizing radiation therapy applied prior to or shortly after angioplasty. Vascular brachytherapy using radioactive sources has become a new treatment option to prevent restenosis. Radioactive stents disclosed in U.S. Pat. No. 5,059,166 (Fischell et al) or radioactive catheters disclosed in U.S. Pat. No. 5,199,939 (Dake et al) have been introduced to minimize or eliminate neointimal hyperplasia after angioplasty. However, logistic complexities of using radiation sources in coronary arteries and radiation safety issues have prompted researcher to improve the irradiation technology. U.S. Pat. No. 5,951,458 (Hastings et al) discloses a radiation catheter that releases oxidizing agents such a $H_2O_2$ to prevent restenosis after cardiovascular interventions. The method described by Hastings helps to reduce radiation doses or treatment times necessary for a radioactive treatment to prevent restenosis.

Oxygenated fluorocarbons emulsions have been used to treat hypoxic and ischemic disorders. Oxygen-transferable fluorocarbon emulsions become known as artifical blood substitutes more than twenty years ago. In U.S. Pat. No. 3,958,014 and U.S. Pat. No. 4,252,827, fluorocarbon emulsion are disclosed that have a small particle size of 0.02 to 0.25 microns, and are injectable into the blood stream. In U.S. Pat. No. 4,445,500, Osterholm teaches that oxygenated fluorocarbon emulsions can be injected into the cerebrospinal pathway to improve aerobic respiration of tissue. U.S. Pat. No. 4,795,423 (Osterholm) discloses an intraocular perfusion with perfluorinated substances to treat ischemic retinopathy.

The local delivery of drugs during an angioplasty procedure using fluids injected into organs via catheters for treatment purpose has been disclosed previously. U.S. Pat. No. 4,636,195 (Wolinsky) teaches that substances may be injected to the vessel wall through a porous balloon catheter. However, the injection of substances into the walls of blood vessels may cause damage of vascular structures during the injection process. The damage of the vessel wall during initial treatment may promote neointimal hyperplasia as a cause of stenosis. Even modified surfaces of infusions balloons with dimples as disclosed in U.S. Pat. No. 6,048,332 may not completely prevent vascular injury during injection therapeutic agents at the time of balloon inflation.

SUMMARY OF THE INVENTION

This invention consists of a oxygen delivery source for the treatment of cardiovascular diseases that allows the local diffusion of a liquid oxygen carrier into blood and tissue, and is capable of oxygenating blood and tissue. The invention is characterised by a porous structure being part of a medical device which is impregnated with an oxygenated fluorocarbon solution. The release kinetics of the solution from the structure are modulated by controlled temperature changes of the environment. The impregnated substrate is sealed with a protecting housing made of plastic or metal allowing storage of the device without the loss of gas and liquid. One of the goals of the invention is to improve oxygen supply to ischemic organs during an angioplasty procedure. For instance, the invention is used to prolong balloon inflation time during high risk PTCA procedures such as balloon or stent treatment of trunk of left main coronary artery. Furthermore, the invention disclosed herein is conceived to be applied for reduction of restenosis of an angioplasty procedure. The invention presented here discloses a novel concept for an angioplasty procedure (including a stent implantation) by improving not only acute safety of the procedure but also the long-term outcome. The major component of this invention is the local delivery of oxygen via an oxygenated fluorocarbon solution into tissue and into blood from percutaneously applicable device. The oxygen eluting carrier is released to the target area from a part of a catheter such as a membrane, a tube, a balloon, a perfusion balloon or a wire. The device presented here allows local diffusion of an oxygen carrier into a hypoxic target tissue, where oxygen is released from the carrier and increases the oxygen tension of the target tissue. During manufacture of polymers for the purpose of medical use, porosity of the basic polymer material is induced in the range of 20 to 200 microns. Alternatively, porous films may be firmly attached to the non-porous surfaces. It is disclosed herein that the microporous material is impregnated with a liquid oxygen carrier. Perfusion channels carrying liquids around the therapeutic device are designed to allowing perfusion of warm or cold liquids to the area of release of the liquid oxygen carrier. The induced local temperature changes fasten or slow down the local release of the solution from the carrier membrane. Polymer tubes impregnated with oxygenated fluorocarbon solutions may be used to supplement oxygen delivery to the blood during a cardiopulmonary bypass procedure. Modified stent delivery balloons, i.e. balloon catheters with a pre-mounted stent or perfusion balloons are the preferred embodiments of the invention. Endovascular stents themselves may also be coated with a thin film membrane incorporating the oxygenated fluorocarbon solution. For restenosis prevention, local delivery of oxygenated fluorocarbon solution is conceived to be combined with the application of ionizing radiation or low energy ultraviolet light to increase the production of oxygen free radicals in the target cell of arterial wall. The effect of increased oxygen free radical production of the proliferating target cell in the arterial wall is DNA damage, which will cause a reduction of restenosis formation. Several other clinical applications related to the field of vascular medicine are suggestive for a therapeutic device that provides local tissue oxygenation. Wound healing of skin lacerations in patients with peripheral occlusive arterial disease and impaired blood flow in the lower limb organs may be significantly improved with the local delivery of an oxygenated fluorocarbon solution via a skin patch placed onto the ischemic skin. These oxygenated tissue patches promotes the growth of new blood vessels into the area of ischemia, for instance in surgically opened wounds. Gangrenes of the lower limb due to arteriosclerosis may be reduced in size.

In the preferred embodiment, the oxygen delivery substrate is located on the surface of a balloon of an angioplasty catheter. The oxygen delivery substrate consists of a porous polymer at a thickness between 20 and 200 μm being integrated into the balloon structure or being wrapped around the balloon. The thin film polymer membrane contains an oxygenated fluorocarbon solution (liquid oxygen carrier). The substrate is sealed with a housing preventing premature release of the treatment substance. Prior to the intended angioplasty procedure, the housing is removed from the device, and it is advanced into the blood circulation. At the site of intervention, the substrate may be brought in contact with the vessel wall. Release kinetics of said liquid oxygen carrier are modified by changes of local temperatures between 0-50° Celsius, for instance by means of injection of cold and warm fluids via the guiding catheter prior to inflation of the balloon. The oxygen enters the blood vessel wall by diffusion. Contact of the device with the target tissue improves oxygen delivery. The local increase in oxygen molecules creates an excess of oxygen free radicals when either ionizing radiation with beta-particle emitters such as Sr-90/Y-90 or P-32 or using ultra-violet light is applied to the target area. A simultaneous application of the oxygenated fluorocarbon solution with the vessel irradiation using ionizing radiation or ultraviolet light is the preferred treatment modality for restenosis prevention. The capacity of oxygen saturation of end organ increases with the improvement of blood flow. Therefore, in another embodiment, the oxygen carrier is released from of a perfusion balloon catheter. The perfusion balloon catheter provides flow of blood from the proximal end of the occluding balloon into the vascular bed distal to the blockage, and thus increases the distribution of the oxygenated fluorocarbon solution to the end organ. Perfusion of blood through the occluded balloon is permitted and the blood will be oxygenated at the distal end of the balloon behind the blood flow blockage. In yet another embodiment, the oxygen delivery source is delivered from the substrate which is part of a coronary wire. The distal tip of a coronary wire is coated with the membrane carrying the liquid fluorocarbon solution or is modified such that the oxygen carrier membrane forms a tube around a retrievable metallic core of the wire. The wire is placed in the distal coronary artery, the core is retrieved and the tube carrying the oxygen source is floating in the blood stream. Thereafter, a conventional balloon catheter is advanced over the wire to treatment zone proximal to the oxygen delivery source and a prolonged balloon inflation can be performed without inducing myocardial ischemia. In another embodiment, the metallic wire is porous. The wire is impregnated with the liquid oxygen carrier at its distal tip. In yet another embodiment, the distal tip of the wire forms a plastic thread which is tightly connected to the metallic portion of the wire.

BRIEF DESCRIPTION OF THE DRAWINGS

FIG. 2 is a schematic longitudinal view of a balloon catheter with an inflated balloon serving as the substrate source for a liquid oxygen carrier in accordance with the present invention.

FIG. 3 is a schematic longitudinal view of an perfusion balloon catheter serving as the substrate source for a liquid oxygen carrier. In this embodiment, a oxygen delivery source membrane is located on the surface of the balloon and proximally and distally to the balloon end on the shaft of the catheter, and is penetrated by holes for the contact with blood flowing through the balloon.

DETAILED DESCRIPTION OF THE DRAWINGS

Figure 1:
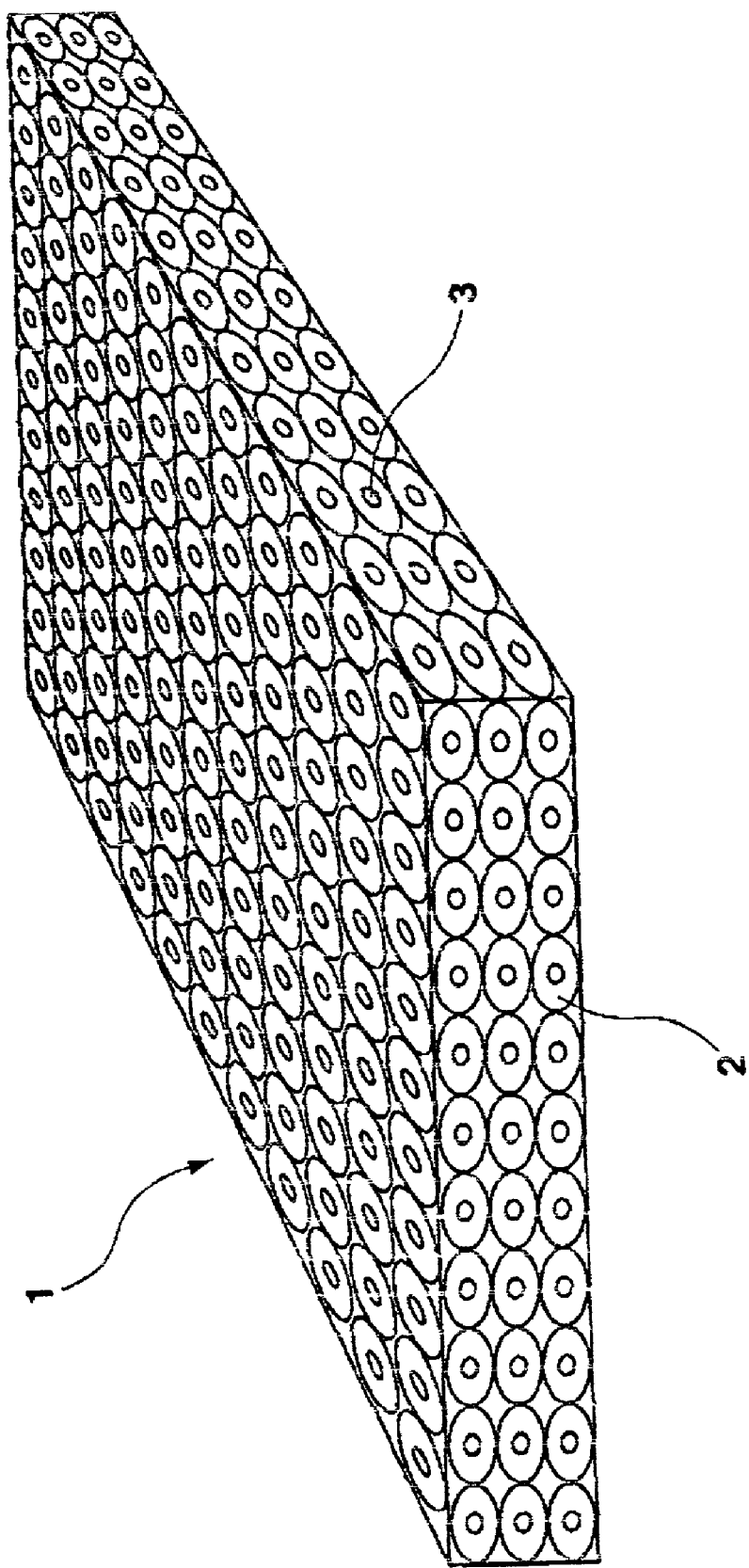
FIG. 1 is a schematic perspective view of a microporous thin film membrane being part of a medical device. The pores function as the flexible substrate for the liquid oxygen carrier in accordance with the invention described herein. The thin film membrane may be used as tissue patch for the improval of closure of wounds.

FIG. 1 shows a perspective view of a porous thin film membrane (1) with pores (2) functioning as a flexible substrate for a liquid oxygen carrier (3) in accordance with the present invention. An oxygenated fluorocarbon solution is incorporated in the substrate and elutes from the substrate. The liquid oxygen carrier diffuses freely out of the thin film membrane. Studies on the release kinetics of the oxygenated fluorocarbons from different polymer membrane show that elution of the oxygenated fluorocarbon solution from such a membrane into tissue or blood varies between minutes and several hours depending on the temperature of the environment. Polymers with small pore sizes of 20-200 μ are preferable produce an effective incorporation for oxygenated fluorocarbon solutions. The temperature-dependent release feature of the membrane is used for all the vascular devices described herein such as tubes, balloons, endovascular stents, wires, or tissue patches aimed at modifying oxygen supply tissues of body organs. Generally, the release kinetics from the substrate are controlled by injection of fluids of 0-50° Celsius making direct or indirect contact with the substrate carrying the oxygenated fluorocarbon solution.

FIG. 2 shows a schematic longitudinal view of a balloon catheter (4) with an inflated balloon (5) serving as the substrate source (6) for the liquid oxygen carrier, whereas the source is tightly connected with the balloon (5). The liquid oxygen carrier is incorporated into a membrane (7) with is attached to the surface of the balloon. The liquid oxygen carrier is a oxygenated fluorocarbon solution. A "guide-wire" lumen (8) allows positioning of the balloon in the artery with a wire. This guide-wire may be a flexible wire (25) emitting ionizing radiation (26) from incorporated beta-particle emitters such as Sr-90NY-90 (strontium/yttrium) or P-32 (phosphorus) or ultraviolet light (UV) waves (27). In the first case, the flexible wire (25) may be partly coated with the beta-particle-emitters (26) and in the latter case, the flexible wire (25) is an ultraviolet light waveguide connected to an ultraviolet light source and having a surface structure within the balloon (5) to radially emit the UV waves (27). The shaft of the catheter (9) includes an inflation channel (10) for inflation of balloon with fluids or contrast agents to visualise the balloon under fluoroscopy.

FIG. 3 shows a schematic longitudinal view of an perfusion balloon catheter (11) serving as the substrate source (6) for the liquid oxygen carrier. In this embodiment, the oxygen delivery source membrane (7) is located on the surface of the balloon (5) and proximally (12) and distally (13) to the balloon end of the catheter (11) on the shaft (9) of the catheter. The shaft (9) of the perfusion balloon catheter includes the guide wire lumen (8), a balloon inflation lumen (14), and a perfusion fluid lumen (15). The perfusion fluid lumen (15) allows perfusion of blood or transport of therapeutic fluids (temperature between 0-50° C.) through the inflated balloon. The perfusion fluid lumen (15) is designed provides means for allowing injection of therapeutic liquids or drugs with temperatures between 0 and 50° C. to modify the release kinetics of the oxygen carrier from the substrate. Holes beyond the proximal end (16) of the balloon connect a pathway for blood through the shaft (9) of the perfusion balloon catheter to the distal end of the catheter (17). The perfusion fluid lumen (15) connects to the holes at the proximal (16) and distal end (17) of the balloon. The perfusion holes (16, 17) are penetrating through the membrane (12, 13) carrying the liquid oxygen carrier. Thus, blood perfusion through the balloon carries blood that is oxygenated by the membrane at the proximal end of the inflated balloon and is oxygenated beyond the distal end of the inflated balloon by the membrane after passage through the balloon. The guide wire (25) contains the liquid oxygen carrier (7) at its distal tip (28). A stent (29) is mounted on the deflated balloon (5). Upon inflation of the balloon via its lumen (14), the stent (29) is expanded and deployed into the vessel.

Figure 4:
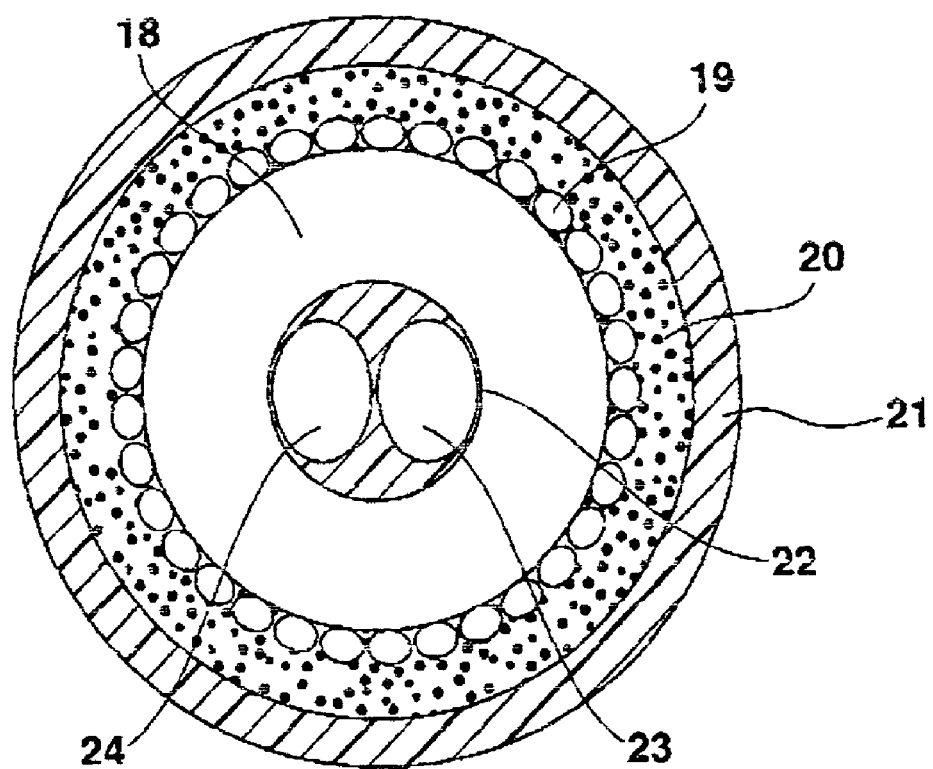
FIG. 4 is a schematic cross-sectional view of the distal part of a medical device containing a liquid oxygen delivery source being encompassed by a housing sealing off the source in accordance with the present invention.

FIG. 4 shows a schematic cross-sectional view of a medical device containing a liquid oxygen delivery source being encompassed by a removable housing sealing off the impregnated source in accordance with the present invention. The oxygen delivery source such as a perfusion balloon catheter (18) with an attached thin film membrane (19) incorporating the oxygen carrier is placed in an container (21) filled with a liquid oxygen carrier solution (20). The container eliminates any dissipation of liquid or oxygen, and is sought to be a storage place for the oxygen delivery source. The inner part (22) of the shaft of the perfusion catheter contains a guide wire lumen (23) and perfusion fluid lumen (24) for the perfusion of blood or therapeutic fluids.

The invention described herein consists of an oxygen delivery source for local blood or tissue oxygenation. The invention consists of porous polymer structures being part of a medical device from which a liquid oxygen carrier is locally or systemically released. The substrate membrane impregnated with the oxygen carrier may be a part of a tube, a balloon, a perfusion balloon, a stent and of a wire. The substrate membrane is sealed with a removable housing for the oxygen carrier to allow storage of the medical device.

We claim:

1. A system comprising:
   a hollow tube having a distal end, a proximal end, and a lumen extending between the distal end and the proximal end;
   at least a portion of the tube comprising a porous membrane; and
   an oxygenated fluorocarbon solution incorporated in the porous membrane;
   wherein the porous membrane has a porosity in the range of 20-200microns, in order that:
   (i) the oxygenated fluorocarbon solution is effectively incorporated into the porous membrane; and
   (ii) when the porous membrane is positioned in blood, the oxygenated fluorocarbon solution elutes out of the porous membrane, with the elution of the oxygenated fluorocarbon solution into the blood varying between minutes and several hours, depending on the temperature of the environment.

2. A system according to claim 1 wherein at least a portion of the porous membrane is located within the hollow tube.

3. A system according to claim 1 wherein at least a portion of the porous membrane is located on an outer surface of the hollow tube.

4. A system according to claim 1 wherein the hollow tube and the porous membrane are configured so that liquid may pass through the porous membrane as it exits and enters the lumen.

5. A system according to claim 1 wherein the hollow tube comprises an inflatable balloon.

6. A system according to claim 5 wherein the porous membrane is mounted to a surface of the balloon.

7. A system according to claim 5 wherein the hollow tube and inflatable balloon are in the form of a balloon catheter.

8. A system according to claim 5 further comprising a removable housing disposed around the porous membrane.

9. A system according to claim 1 wherein the hollow tube further comprises a plurality of holes formed in the sidewall of the hollow tube and communicating with the lumen of the hollow tube, and further wherein the porous membrane is disposed adjacent to the plurality of holes.

10. A system according to claim 1 wherein the system further comprises a coronary wire.

11. A system according to claim 10 wherein a tip of the coronary wire comprises a porous membrane, wherein an oxygenated fluorocarbon solution is incorporated in the porous membrane, and further wherein the porous membrane has a porosity in the range of 20-200 microns, in order that:
   (i) the oxygenated fluorocarbon solution is effectively incorporated into the porous membrane; and
   (ii) when the porous membrane is positioned in blood, the oxygenated fluorocarbon solution elutes out of the porous membrane, with the elution of the oxygenated fluorocarbon solution into the blood varying between minutes and several hours, depending on the temperature of the environment.

12. A system according to claim 10 wherein the coronary wire further comprises an ionizing radiation source.

13. A system according to claim 12 wherein the ionizing radiation source comprises a beta-particle emitter.

14. A system according to claim 10 wherein the coronary wire further comprises an ultraviolet light source.

15. A system according to claim 1 wherein the porous membrane comprises a porous polymer.

16. A system according to claim 15 wherein the porous polymer is selected from the group consisting of Teflon, polyethylene, polyethylene terephtalate, nylon, silicon, and cellulose acetate.

17. A system according to claim 1 wherein the porous membrane is lipophilic.

18. A system according to claim 1 wherein the system further comprises a housing for protectively covering the porous membrane in order to prevent the loss of the oxygenated fluorocarbon solution and/or oxygen.

19. A system according to claim 1 wherein the system further comprises a fluid for passage through the lumen, and further wherein the fluid is at a temperature of between about 0° C and about 50° C.

20. A system according to claim 1 wherein the hollow tube further comprises a stent.

21. A system according to claim 1 wherein the lumen of the hollow tube is configured to modulate release kinetics of the oxygenated fluorocarbon solution by enabling fluid injection at temperatures between about 0° C. and about 50° C..

22. A system comprising:
   a coronary wire;
   at least a portion of the coronary wire comprising a porous membrane; and
   an oxygenated fluorocarbon solution incorporated in the porous membrane;
   wherein the porous membrane has a porosity in the range of 20-200 microns, in order that:
   (i) the oxygenated fluorocarbon solution is effectively incorporated into the porous membrane; and
   (ii) when the porous membrane is positioned in blood, the oxygenated fluorocarbon solution elutes out of the porous membrane, with the elution of the oxygenated fluorocarbon solution into the blood varying between minutes and several hours, depending on the temperature of the environment.

23. A method for treating a patient, comprising: providing:
   (i) a hollow tube having a distal end, a proximal end, and a lumen extending between the distal end and the proximal end, at least a portion of the tube comprising a porous membrane; and
   (ii) an oxygenated fluorocarbon solution; loading the oxygenated fluorocarbon solution into the porous membrane; and
   positioning the tube in the vascular system of the patient so that porous membrane is exposed to blood;
   wherein the porous membrane has a porosity in the range of 20-200 microns, in order that:
   (i) the oxygenated fluorocarbon solution is effectively incorporated into the porous membrane; and
   (ii) when the porous membrane is positioned in blood, the oxygenated fluorocarbon solution elutes out of the porous membrane, with the elution of the oxygenated fluorocarbon solution into the blood varying between minutes and several hours, depending on the temperature of the environment.

* * * * *